United States Patent [19]

Miller

[11] 4,440,183

[45] Apr. 3, 1984

[54] ANATOMICAL DEVICE

[76] Inventor: Jess Miller, Rte. 13, P.O. Box 183B, Fort Worth, Tex. 76119

[21] Appl. No.: 187,486

[22] Filed: Sep. 16, 1980

Related U.S. Application Data

[63] Continuation-in-part of Ser. No. 110,354, Jan. 7, 1980, abandoned.

[51] Int. Cl.³ .............................................. A61F 5/00
[52] U.S. Cl. ..................................................... 128/79
[58] Field of Search ................. 128/79, 341, 261, 343, 128/98

[56] References Cited

U.S. PATENT DOCUMENTS

| | | | |
|---|---|---|---|
| 609,614 | 8/1898 | Doty | 128/79 UX |
| 764,801 | 5/1903 | Emerson | 128/79 |
| 1,511,572 | 10/1924 | Marshall | 128/79 |
| 2,264,934 | 12/1941 | Cronk | 128/79 |
| 2,468,348 | 4/1949 | Shore | 128/341 |
| 3,568,670 | 3/1971 | Gaylord, Jr. | 128/DIG. 15 |
| 3,794,020 | 2/1974 | Bagby | 128/79 |
| 3,799,157 | 3/1974 | McIntire | 128/79 |

FOREIGN PATENT DOCUMENTS

| | | | |
|---|---|---|---|
| 1655 | 2/1869 | France | 128/79 |
| 2052266 | 1/1981 | United Kingdom | 128/79 |

Primary Examiner—Gregory E. McNeill
Attorney, Agent, or Firm—Wofford, Fails & Zobal

[57] ABSTRACT

A device to be fitted around the penis of a human male to facilitate and maintain an erection. In one embodiment, the device is attached to a garment to be worn by the person to hold the device in place around the penis and next to the body. In another embodiment, the device is formed by a folded wire like member the ends of which are spread apart to form supporting arms to be fitted around the waist or hips of the person. In a further embodiment, a belt, adapted to be secured around one's waist, is attached to the wire-like member for holding it in place.

9 Claims, 17 Drawing Figures

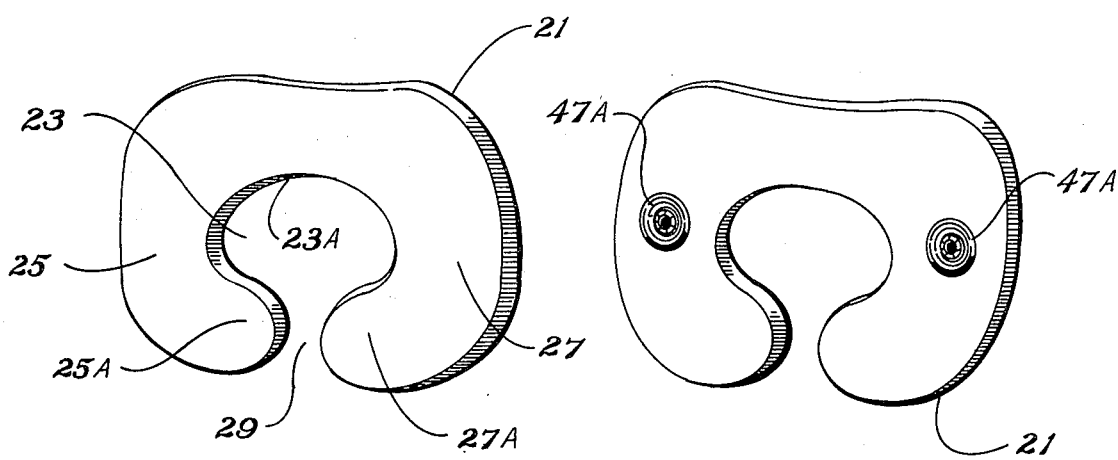
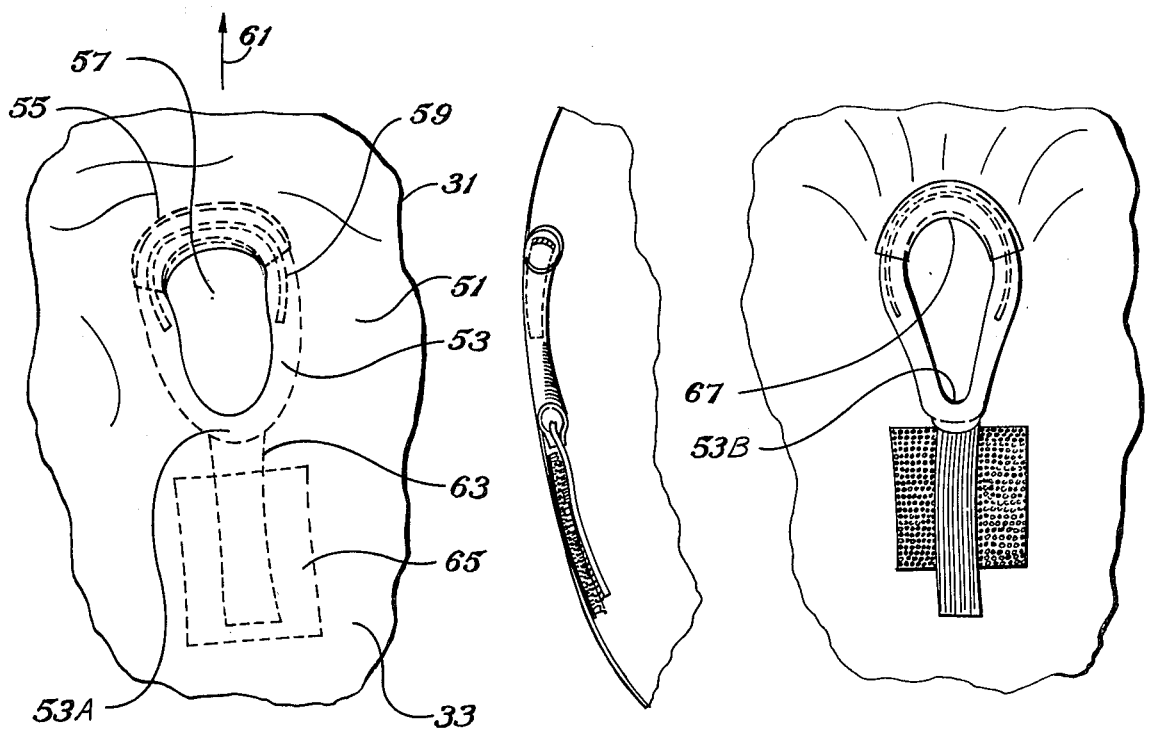

ANATOMICAL DEVICE

This application is a continuation-in-part of U.S. Patent Application Serial No. 110,354, filed January 7, 1980 now abandoned.

SPECIFICATION

1. Field of the Invention

The present invention relates to a device for facilitating and maintaining an erection of the penis of a human male.

2. Description of the Prior Art

U.S. Pat. Nos. 3,794,020, 3,759,253, 3,636,948, 3,461,863, 3,455,301, and 2,581,114 disclose ring shaped or U-shaped devices to be fitted around the penis of a human male for facilitating and maintaining the erection of the penis. These devices, however, have disadvantages in that there is nothing to hold them in place whereby they may shift in position making them ineffective or causing them to be uncomfortable or to interfere with the sexual act.

SUMMARY OF THE INVENTION

It is an object of the present invention to provide a device for facilitating and maintaining an erection of the penis of a human male which does not have the aforementioned disadvantages of the prior art devices.

The device of the present invention comprises an engaging means to be fitted around and engage at least part of the base of the penis for restricting the flow of blood from the penis to achieve and maintain an erection. Support means coupled to said engaging means is adapted to be worn by the person for holding said engaging means in a desired position next to the body.

In one embodiment, the device is attached to a garment to be worn by the person to hold the device in place next to the body.

In another embodiment, the device is formed by a folded wire-like member, the ends of which are spread apart to form supporting arms to be fitted around the waist or hips of the person.

In a further embodiment, a belt, adapted to be secured around one's waist, is attached to the wire-like member for holding it in place.

BRIEF DESCRIPTION OF THE DRAWINGS

FIG. 3 is a device to be inserted in a pocket of the garment of FIG. 1.

FIG. 4 is a device to be attached by snaps to the garment of FIG. 2.

FIG. 5 illustrates another embodiment of the present invention.

FIG. 6 is a side view of FIG. 5.

FIG. 7 is an inside view of the device of FIG. 5 adjusted to a tightened position.

DESCRIPTION OF THE PREFERRED EMBODIMENT

Figure 1:
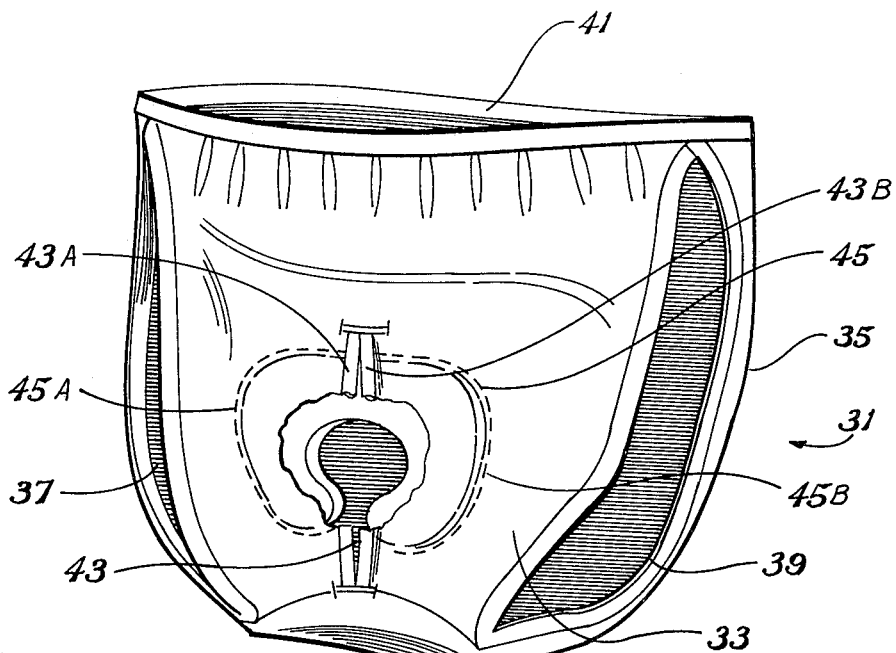
FIG. 1 illustrates one embodiment of the present invention.

Referring now to FIGS. 1 and 3, there is illustrated a generally planar type device 21 to be fitted around the penis of a human male for facilitating and maintaining an erection. The device comprises a generally U-shaped member having a central opening 23 for receiving the penis. The legs 25 and 27 of the device curve inward at 25A and 27A with a lower gap 29 therebetween. When fitted in place, the device 21 will be located next to the body with the penis inserted through opening 23 such that the top edge 23A of opening will engage the top portion of the penis and the clamping extension 25A and 27A will engage the underside of the penis next to and on each side of the uretha. The gap 29 allows the free flow of fluid through the uretha on the under side of the penis. The flattened upper curvature 23A of the upper edge of the opening 23 applies pressure to the top side of the penis and hence to the dorsal vein of the penis and restricts the flow of blood out of the penis back into the body thus creating engorgement of the erectile cells of the penis. Hence the device facilitates and maintains an erection.

Referring to FIG. 1, a garment or harness 31 is provided in order to hold the device securely in the desired position around the base of the penis against the body while in use. The garment 31 is formed of natural or synthetic fibers and comprises front and back sides 33 and 35 with two openings 37 and 39 for the legs and a top opening 41 for the waist. A front opening 43 is provided for the penis. A pocket 45 attached to the inside of the front side 33 is provided for holding the device as shown in FIG. 1 with the opening 23 in alignment with the front opening 43. The pocket 45 comprises two halves 45A and 45B each with a side opening (not shown) along edges 43A and 43B respectively of the garment which define the front opening 43. The side openings of the pocket allow the device 21 to be inserted in the pocket 45 and removed therefrom. Thus device 21 having different size openings 23 may be located in the pocket 45 of the garment or harness 31. The device 21 may be formed of molded plastic, molded fiber (such as paper), synthetic rubber of suitable density and elasticity, etc.

Thus as can be understood, the device 21 when secured to the garment 31 will be held in the desired position around the base of the penis next to the body whereby it will not shift in position or interfere with the sexual act.

Figure 2:
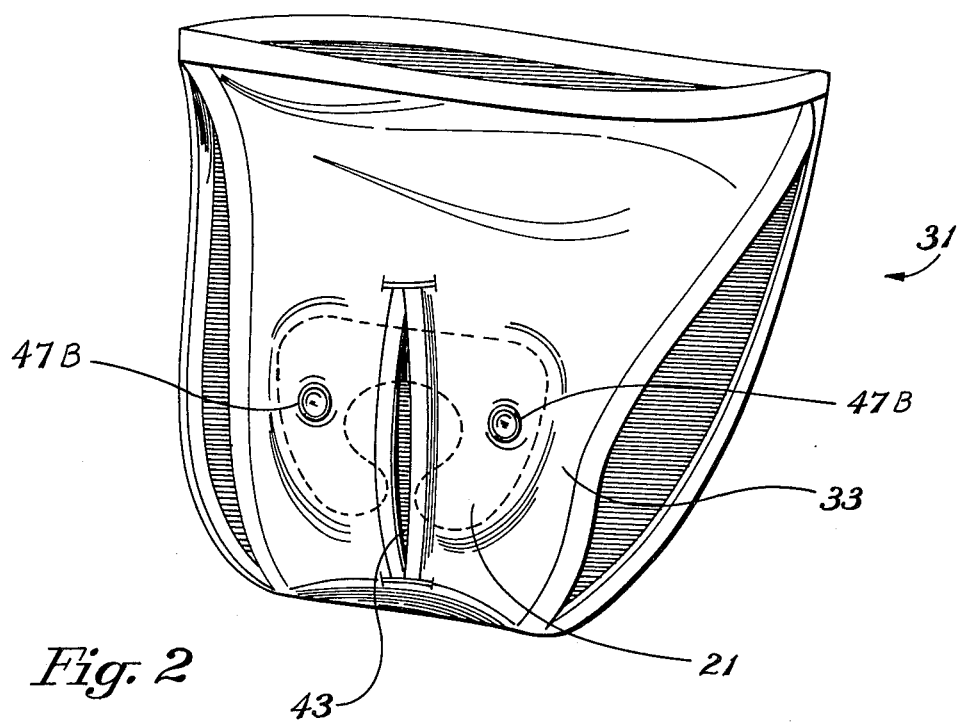
FIG. 2 illustrates another embodiment of the present invention.
Figure 9:
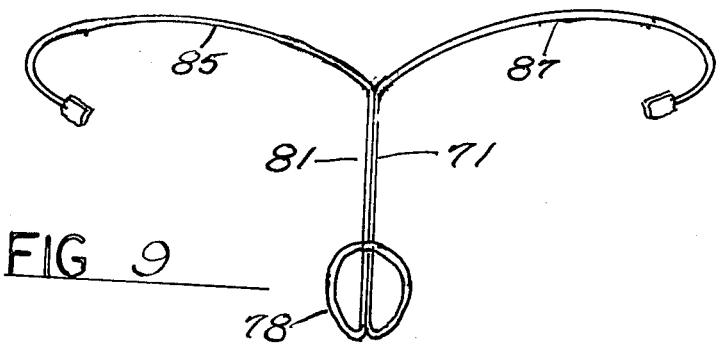
FIG. 9 is a view of FIG. 8 taken along lines of 9—9 thereof.

The embodiment of FIGS. 2 and 4 is similar to that of FIGS. 1 and 3 except that the device 21 is secured in place by snaps 47A and 47B attached to the device 21 and to the garment 31.

In the embodiment of FIGS. 5-7, the device for facilitating and maintaining an erection is identified at 51. It comprises a resilient ring shaped member 53 having an upper collar 55. The member 53 and collar 55 are attached to the front side 33 of the garment 31 such that the opening 57 formed through the ring shaped member coincide with the front opening formed through the front side 33 of the garment. The purpose of the collar 55 is to increase the rigidity at the top. Member 59 is a flexible steel pin inserted in member 53 at its top to increase rigidity at the top, however, pin 59 may not be needed in view of collar 53. The upper end of the front side of the garment is in the direction of arrows 61. Attached to the lower end 53A of the ring 53 is a VELCRO strip 63 adapted to be adjustably attached to VELCRO strip 65 sewn to the garment. In use, the penis is inserted through the opening 57 and the VELCRO strip 63 pulled down a desired amount for engagement with the strip 65 as seen in FIG. 7 to apply the desired amount of pressure to the top side of the penis and hence to the dorsal vein by surface 67 of collar 55, thus restricting the flow of blood from the penis and creating engorgement of the erectile cells of the penis. The lower surface 53B of ring shaped member 53 will be out of engagement with the penis, thereby not affecting the free flow of fluid through the uretha. The garment 31 will maintain the ring 53 and collar 55 in place around the base of the penis next to the body whereby it will not shift in position or interfere with the sexual act.

The embodiment of FIGS. 8-11 comprises a wire like member 71 which is folded at its center 73 to form two branches of 75 and 77 which curve away from each other and together to form a loop 78 with an opening 79 for receiving the penis. The two branches then extend adjacent each other defining a central portion 81 which extends rearward and upward. At point 83 the two branches extend away from each other in a forward direction at 85 and 87. In use, the penis is inserted through opening 79 with the central portion 81 located between the legs and the crotch, extending rearward toward the lower part of the back where arms 85 and 87 split and extend forward and are clamped around the waist or above the pelvis, clamping the device to the body. Knobs 89 and 91 prevent the ends of the device from scratching the body. The arms 85 and 87 hold the loop 88 securely in place around the penis without going far enough around the body to be offensive to the sexual partner thereby allowing the user full freedom of movement.

The penis opening 79 is shaped to fit all sizes and angled in relation to the body to allow pressure to be applied by surface 93 to the top side of the penis and hence to the dorsal vein thus restricting the flow of blood from the penis and creating engorgement of the erectile cells of the penis. The lower surfaces 95 of the loop 80 do not engage the penis thereby allowing free flow of fluid through the uretha. The loop 78 presses further back into the body area of the penis to create more stability of erection by affording greater length of erectile cell engorgement by pressing back into the tissue cavity surrounding the penis as it extends from the area of the prostate. The area of pressure applied to the dorsal vein of the penis can be as much as one inch behind the straight face of the body with normal extension of the surrounding skin. Thus the device applies pressure to the dorsal vein well back of the straight face surface of the body adjacent the penis.

The device 71 may be made of plastic or metal of suitable strength and elasticity.

Figure 12:
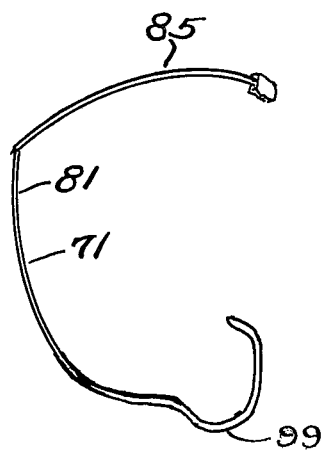
FIG. 12 is a side view of a modification of the device of FIG. 8.
Figure 10:
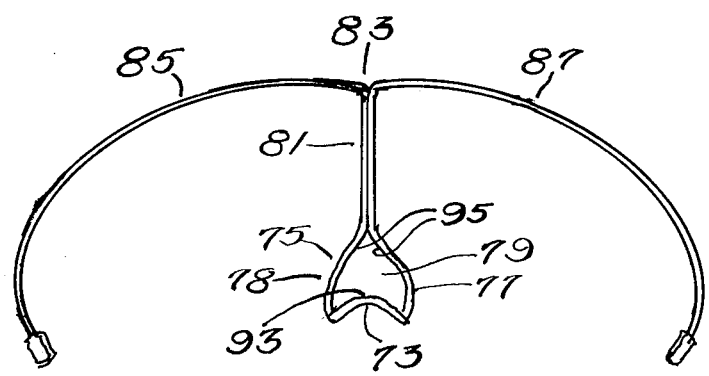
FIG. 10 is a view of FIG. 8 taken along the lines 10—10 thereof.
Figure 8:
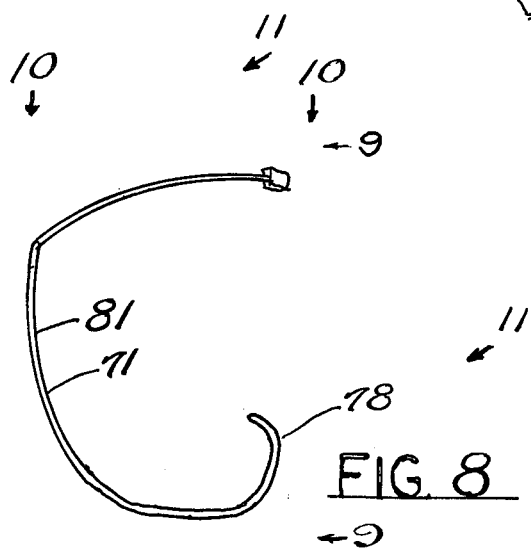
FIG. 8 is another embodiment of the present invention.
Figure 11:
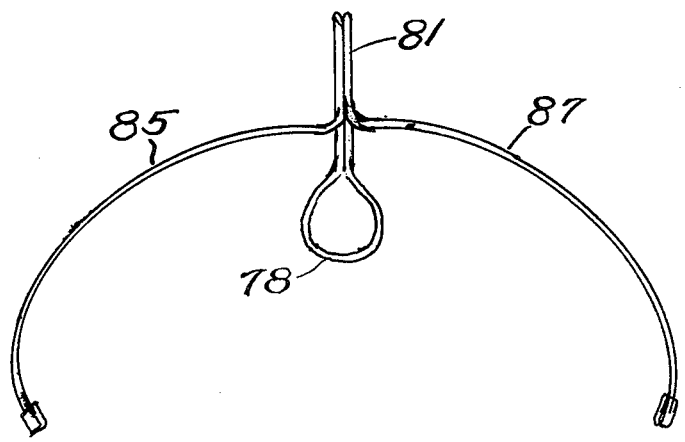
FIG. 11 is a view of FIG. 8 taken along the lines 11—11 thereof.

The device 71 of FIG. 12 is the same as that of FIGS. 8-11 except that the loop 78 and the central portion 71 next to the loop are bent downward at 99 to provide room for the scrotum.

Figure 13:
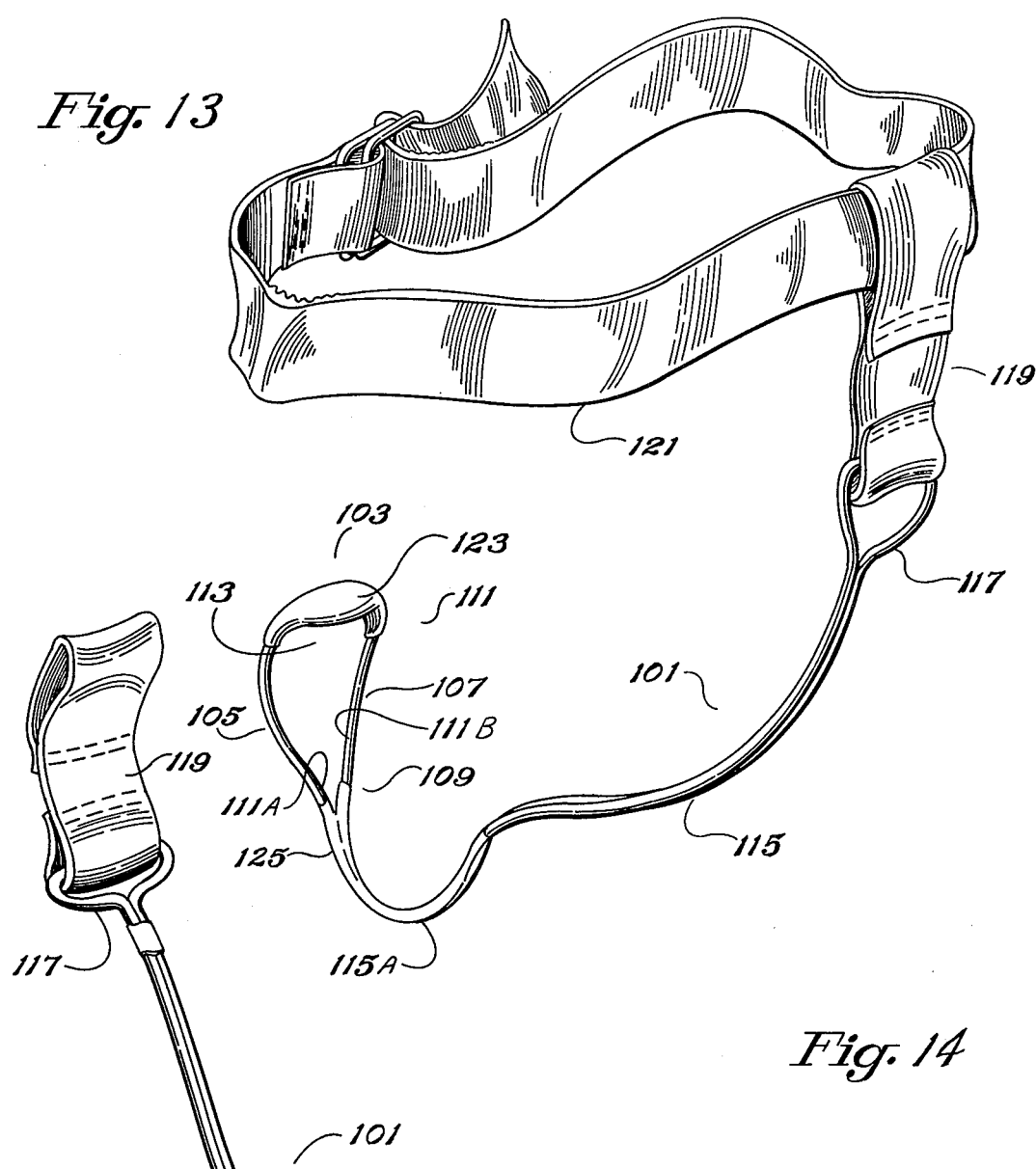
FIGS. 13 and 14 illustrate other embodiments of the present invention.

The embodiment of FIG. 13 comprises a wire like member 101 which is folded at its center 103 to form two branches 105 and 107 which curve away from each other and together at 109 to form a loop 111 with an opening 113 for receiving the penis. From point 109, the two branches extend adjacent each other defining a central portion 115 which extends rearward and upward. At the opposite end of central portion 115, a loop 117 is formed for receiving a strap 119 which in turn is adapted to receive a flexible belt 121 to be secured around the waist. Padding material 123 is secured around the top of the loop 111. Padding material 125 also is secured around a portion of the central portion 115 next to the base of the loop 111. In use, the penis is inserted through opening 113 with the central portion 115 located between the legs and crotch, extending rearward toward the lower part of the back. The belt 121 is secured around the waist to hold the central portion 115 between the legs and the loop 111 around the penis next to the body. The lower portion of the padding 123 will engage the top of the penis and apply pressure thereto and hence to the dorsal vein to restrict the flow of blood from the penis to create engorgement of the erectile cells of the penis. The lower surfaces 111A and 111B do not engage the penis and hence will not affect the free flow of fluid from the uretha. The central portion 115 is bent downward at 115A to provide room for the scrotum. The device 101 may be made of plastic or metal of suitable strength and elasticity.

Figure 14:
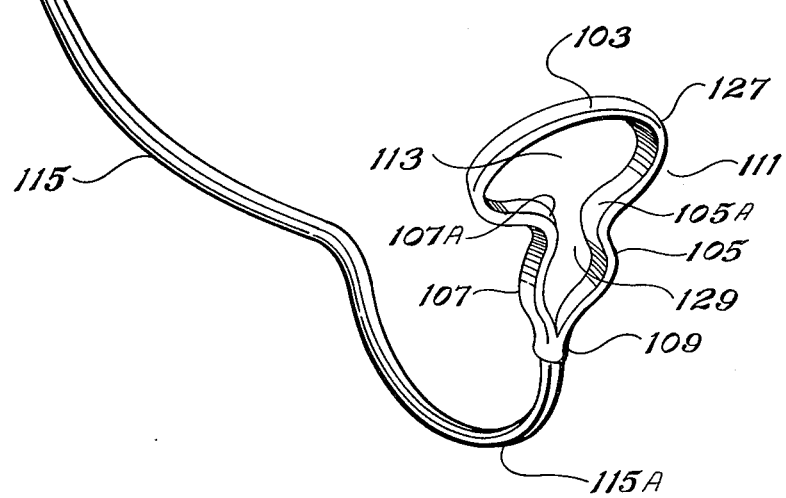

The embodiment of FIG. 14 is similar to that of FIG. 13 and like reference numerals identify like components. In FIG. 14, the belt 121 is not illustrated. In the embodiment of FIG. 14, branches 105 and 107 extend toward each other at 105A and 107B and then away from each other before extending adjacent each other at 109. Padding material 127 is secured around the complete loop. When the penis is inserted into the opening 113, the underside of center portion 103 engages the top of the penis and portions 105A and 107A will engage the underside of the penis next to and on each side of the uretha. The gap 129 allows the free flow of fluid through the uretha on the underside of the penis.

Figure 15:
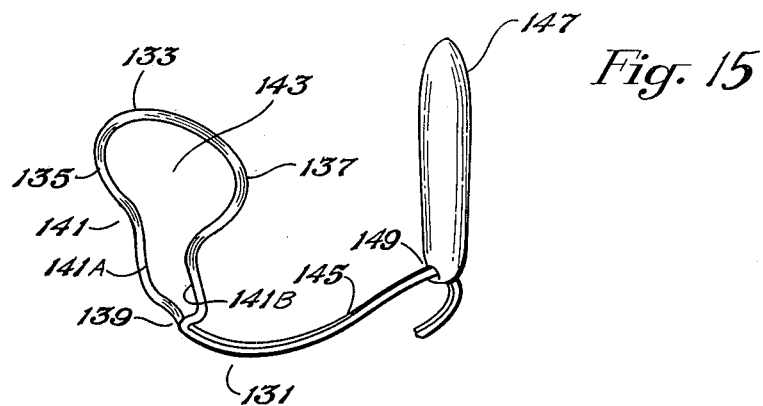
FIGS. 15, 16, and 17 illustrate additional embodiments of the present invention.

The embodiment of FIG. 15 comprises a wire like member 131 which is folded at its center 133 to form two branches 135 and 137 which curve away from each other and together at 139 to form a loop 141 with an opening 143 for receiving the penis. From point 139, the two branches extend adjacent each other defining a portion 145 which extends rearward and upward. A protrusion or knob 147 is coupled to the rear end 149 of portion 145 for insertion into the anus. In use, the penis is fitted into the opening 143, the rearward and upward extending portion 145 is located between the legs and the knob 147 is inserted into the anus. The knob 147, when fitted into the anus holds the portion 145 between the legs and the loop 141 in place around the penis at its base next to the body. The knob 147 when fitted into the anus also provides some sexual stimulation by anal massage. The lower portion of the portion 133 of the loop 141 will engage the top of the penis and apply pressure thereto and hence to the dorsal vein to restrict the flow of blood from the penis to create engorgement of the erectile cells of the penis. The lower surfaces 141A and 141B do not engage the penis and hence will not affect the free flow of fluid from the uretha. A hook 151 is provided for removing the knob 147 from the anus.

Figure 16:
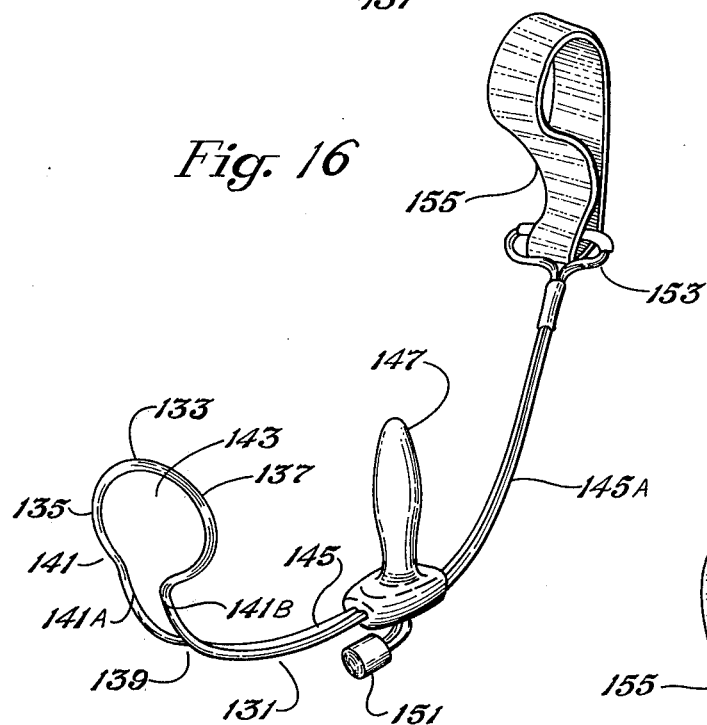

The embodiment of FIG. 16 is similar to that of FIG. 15 except that the portion 145 extends upward beyond knob 147 at 145A. A loop 133 is formed at the end of portion 145 for receiving a strap 155 which in turn is adapted to receive a flexible belt (not shown) to be secured around the waist. The belt provides additional support for holding the loop 141 in place. Wire portions 145 and 145A are partially flexible.

Figure 17:
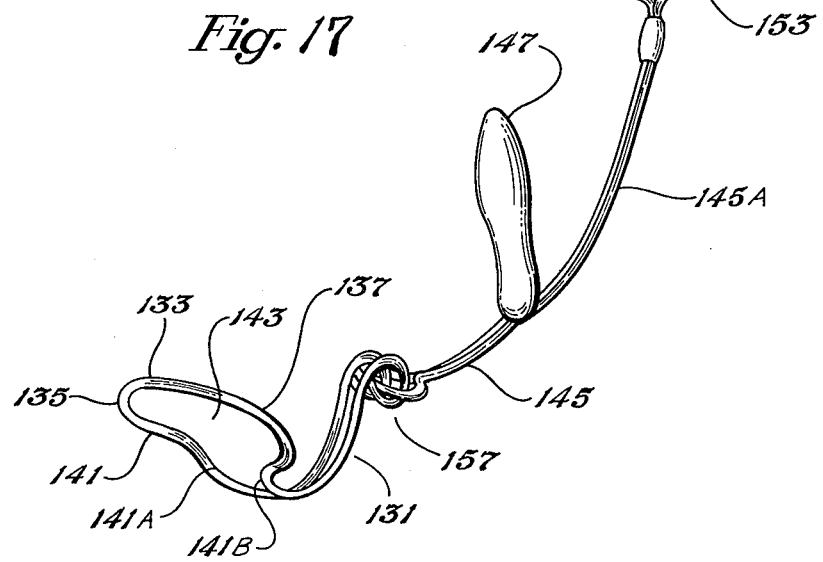

The embodiment of FIG. 17 is similar to that of FIG. 16 except that the loop 141 is hinged at 157 to wire portion 145.

I Claim:

1. A device for facilitating and maintaining the erection of the penis of a human male, comprising:
    a wire-like closed loop-shaped member adapted to be fitted around and engage at least the dorsal part of the base of the penis for restricting the flow of blood from the penis to achieve and maintain an erection,
    a central portion having a first end coupled to said closed loop-shaped member and extending rearward and upward therefrom to an opposite end,
    said central portion constructed from a wire-like material and defining a given non-linear configuration,
    said central portion being adapted to be located between the legs of a human male, and
    means coupled to said opposite end of said central portion for engaging the hips, waist, or the like for holding said central portion between the legs of a human male and said closed loop-shaped member in place around the penis next to the body,
    said central portion being formed of a material sufficient to maintain said central portion in said given non-linear configuration when said central portion is supported at said opposite end.

2. The device of claim 1 wherein:
    said device is formed of a single wire-like member which is folded at its center to form two branches which extend away from each other and then together to form said closed loop-shaped member and extend adjacent to each other to form said central portion.

3. The device of claim 1 wherein said means coupled to said opposite end of said central portion comprises:
    two arms extending outward and forward from said opposite end of said central portion whereby when said central portion is located in place between the legs of a human male, said arms extend from the rear of the human male forward for engaging the hips, waist, or the like for holding the closed loop-shaped member in place around the penis next to the body.

4. The device of claim 1 wherein said means coupled to said opposite end of said central portion comprises:
    two arms extending outward and forward from said opposite end of said central portion whereby when said central portion is located in place between the legs of a human male, said arms extend from the rear of the human male forward for engaging the hips, waist, or the like for holding the closed loop-shaped member in place around the penis next to the body,
    said arms, central portion, and said closed loop-shaped member when seen from the side define a C-shaped configuration.

5. The device of claim 1 wherein:
    said device is formed of a single wire-like member which is folded at its center to form two branches which
    (a) extend away from each other and then together to form said closed loop shaped member,
    (b) extend adjacent to each other to form said central portion, and
    (c) extend away from each other to form said two arms.

6. The device of claim 1 wherein said means coupled to said opposite end of said central portion comprises:
    belt means adapted to be secured around the waist or the like.

7. A device for facilitating and maintaining the erection of the penis of a human male, comprising:
    a closed wire-like loop-shaped member adapted to be fitted around and engage at least the dorsal part of the base of the penis for restricting the flow of blood from the penis to achieve and maintain an erection,
    a central portion having a first end coupled to said closed loopshaped member and extending rearward and upward therefrom to an opposite end,
    said central portion constructed from a wire-like material and defining a given non-linear configuration,
    said central portion being adapted to be located between the legs of a human male,
    said opposite end of said central portion having holding means to which belt means is adapted to be coupled to be secured around the waist or the like for holding said central portion between the legs of a human male and said closedloop-shaped member in place around the penis next to the body,
    said central portion being formed of a material sufficient to maintain said central portion in said given non-linear configuration when said central portion is supported at said opposite end.

8. The device of claim 7 wherein:
    said device is formed of a single wire-like member which is folded at its center to form two branches which extend away from each other and then together to form said closed loop - shaped member and extend adjacent to each other to form said central portion.

9. The device of claim 7 comprising:
    belt means coupled to said holding means.

* * * * *